United States Patent [19]

Cohen

[11] Patent Number: 5,014,698
[45] Date of Patent: * May 14, 1991

[54] METHOD OF AND SYSTEM FOR MONITORING AND TREATING A MALFUNCTIONING HEART

[75] Inventor: Todd J. Cohen, Mountain View, Calif.

[73] Assignee: Leonard Bloom, Towson, Md.; a part interest

[*] Notice: The portion of the term of this patent subsequent to Oct. 4, 2005 has been disclaimed.

[21] Appl. No.: 416,024

[22] Filed: Oct. 2, 1989

Related U.S. Application Data

[63] Continuation-in-part of Ser. No. 385,544, Jul. 27, 1989, Pat. No. 4,984,572, which is a continuation-in-part of Ser. No. 233,367, Aug. 18, 1988, Pat. No. 4,967,749, which is a continuation-in-part of Ser. No. 105,030, Oct. 6, 1987, Pat. No. 4,774,950.

[51] Int. Cl.$^5$ .............................................. A61N 1/00
[52] U.S. Cl. ......................... 128/419 D; 128/419 PG
[58] Field of Search ........ 128/419 D, 419 PG, 419 P, 128/696

[56] References Cited

U.S. PATENT DOCUMENTS

| | | | |
|---|---|---|---|
| 4,562,846 | 1/1986 | Cox et al. | 128/696 |
| 4,770,177 | 9/1988 | Schroeppel | 128/419 PG |
| 4,774,950 | 10/1988 | Cohen | 128/419 D |
| 4,819,662 | 4/1989 | Heil, Jr. et al. | 128/419 P |
| 4,895,151 | 1/1990 | Grevis et al. | 128/419 D |

Primary Examiner—Francis Jaworski
Assistant Examiner—George Manuel
Attorney, Agent, or Firm—Leonard Bloom

[57] ABSTRACT

A system for treating the malfunctioning heart of a patient includes means which derive at least one electrical signal from the patient's heart and means which derive at least one physiologic signal from or related to the patient's circulatory system, a central processing unit with a RAM and a ROM, receives and responds to the at least one electrical signal and to the at least one physiologic signal. Output means controlled by the central processing unit provides corrective measure(s) to the patient. A method of treating the malfunctioning heart of a patient, includes deriving at least one electrical signal from the patient's heart, deriving at least one physiologic signal from or related to the patient's circulatory system, processing the at least one electrical signal and the at least physiologic signal, and providing a corrective measure or measures to the patient whenever a malfunction is identified.

54 Claims, 12 Drawing Sheets

METHOD OF AND SYSTEM FOR MONITORING AND TREATING A MALFUNCTIONING HEART

CROSS REFERENCE TO RELATED APPLICATION

This application is a continuation-in-part of copending application Ser. No. 385,544 of Todd J. Cohen filed July 27, 1989, now U.S. Pat. No. 4,984,572, and entitled "Hemodynamically Responsive System for and Method of Treating a Malfunctioning Heart". The Ser. No. 385,544 is, in turn, a continuation-in-part of copending application Ser. No. 233,367 of Todd J. Cohen filed Aug. 18, 1988, now U.S. Pat. No. 4,967,749, and entitled "Hemodynamically Responsive System for and Method of Treating a Malfunctioning Heart" which is a continuation-in-part of Ser. No. 105,030 of Todd J. Cohen filed on Oct. 6, 1987, now U.S. Pat. No. 4,774,950 and entitled "Hemodynamically Response System for and Method of Treating a Malfunctioning Heart", which has matured as U.S. Pat. No. 4,774,950 granted Oct. 4, 1988. The disclosures of the three prior applications are incorporated herein in their entirety respectively by reference.

BACKGROUND OF THE INVENTION

1. Field of the Invention

This invention relates to a method of and system for treating a malfunctioning heart. The term "hemodynamic parameter", as used herein, means any parameter which may be sensed or determined and either directly or indirectly affects the motion or constituents of blood or performance of the heart within the circulatory system. The invention provides for the cardioverting/defibrillation of a malfunctioning heart, as well as the possibility of overcoming a tachycardia and bradycardia manifestations without resorting to either cardioverting or defibrillating the heart. The invention also may involve sensing and treating asystole, ischemia, early infarction and heart failure.

2. Description of the Prior Art

In recent years, substantial progress has been made in pacemakers and in the development of cardioverting/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U.S. Pat. No. 3,942,536 of Mirowski et al., the technique involving responses to a sensed peak right ventricular systolic pressure dropping to a fixed predetermined threshold level. This known technique did not involve mean pressure changes in either direction from a baseline. Nor did it involve sensing of pressure within any vessels which extends between the heart and lung(s).

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators (AICD) which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. The AICD has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", *Medical Instrumentation,* Vol. 20, pages 285-291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", *JACC,* Vol. 6, No. 2, pages 461-466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One problem with current systems is that they function primarily as a rate-only sensing systems and may fire for nonmalignant as well as malignant tachycardias. These firings are not benign; potentially endangering myocardium, wasting energy and inflicting pain on the conscious patient, all distinct shortcomings and disadvantages.

SUMMARY OF THE INVENTION

The principal object of the present invention is to provide a method of and system for treating a malfunctioning heart which provide for determining the presence of a malfunction and deliver an output to correct or alleviate the malfunction.

A further object of the present invention is to provide a method of and system for treating a malfunctioning heart which is hemodynamically responsive to change in a hemodynamic parameter, such as pressure(s) at one or more sites in the circulatory system of a patient, and to an electrical signal or signals derived from the heart.

From one vantage point, the invention can be seen as being in a system for treating the malfunctioning heart of a patient. Means derive at least one electrical signal from the patient's heart. Other means derive at least one physiologic signal from or related to the patient's circulatory system. A central processing unit, which may be a microprocessor, with its associated RAM and ROM is provided. Means input the at least one electrical signal and the at least one physiologic signal to the central processing unit. Output means controlled by the central processing unit provide a corrective measure or measures to the patient.

From a slightly different viewpoint, the invention can be seen as being in a system for treating the malfunctioning heart of a patient which includes means for deriving at least one electrical signal from the patient's heart and means for deriving at least one physiologic signal from or related to the patient's circulatory system. A central processing unit, associated with a ROM and RAM is provided. Means the at least one electrical signal and the at least one physiologic signal to the central processing unit. Monitoring and/or recording means are associated with the central processing unit to provide indications of the inputs and outputs thereof.

The system may include means for monitoring heart rhythm to develop the at least one electrical signal, and respectively and/or in various combinations means responsive to the at least one electrical signal and to the at least one physiologic signal for identifying stable SVT, unstable SVT, stable VT, unstable VT, stable atrial fibrillation, unstable atrial fibrillation, ventricular fibrillation, asystole, stable bradycardia, unstable bradycardia, ischemia, early infarction and heart failure alone.

In its method aspect, the invention can be viewed as a method of treating the malfunctioning heart of a patient which includes deriving at least one electrical signal from the patient's heart, deriving at least one physiologic signal from or related to the patient's circulatory system, processing the at least one electrical signal and the at least physiologic signal, and providing a corrective measure to the patient whenever a malfunction is identified.

The novel features that are considered characteristic of the invention in its method and system aspects are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

DETAILED DESCRIPTION OF THE PREFERRED EMBODIMENTS

Figure 1:
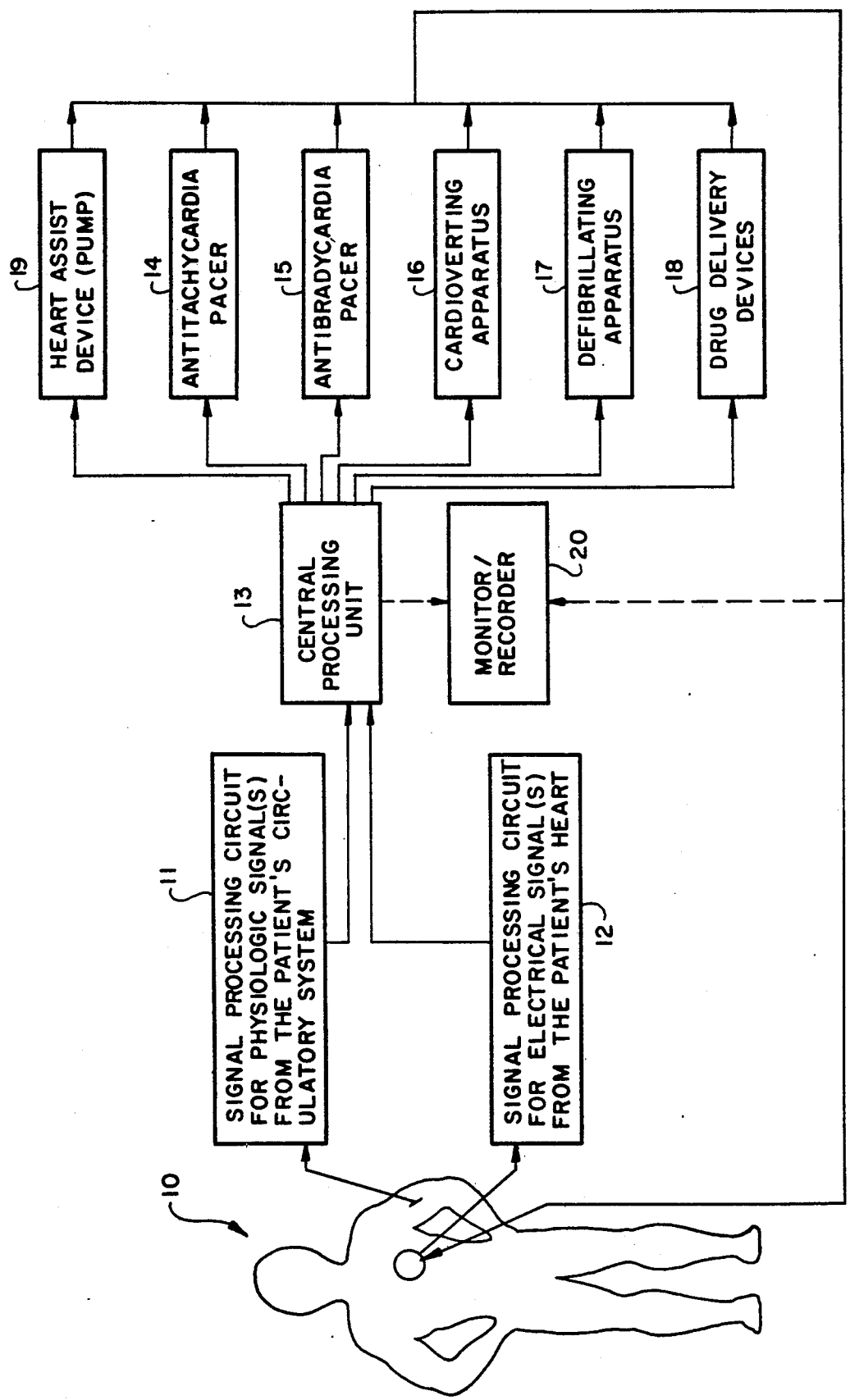
FIG. 1 is a block, generalized illustration of an exemplary, electrical- and physiologic- signal responsive system for treating a malfunctioning heart in accordance with the present invention and which may be used in carrying out the invention in its method aspect.

As illustrated in FIG. 1, an exemplary system for treating a malfunctioning heart of a patient 10 includes a signal processing circuit 11 which receives signals representing a physiologic condition at one or more sites within or related to the circulatory system of a patient. The signal(s) representing the physiologic condition(s) preferably involve hemodynamic parameter(s) at the site(s) and reflect the dynamic nature of the pressure(s) at the site(s). The system also includes a signal processing circuit 12 which receives an electrical signal or signals from the heart of a patient; for example, the circuit 12 may receive an electrical signal or signals obtained by conventional internal or external EKG electrodes and which are processed to derive a signal representing the QRS complex, the R-wave (the beating rate of the heart), a signal or signals related to atrial contractions (or the like) and/or a signal or signals related to ventricular contractions (or the like).

The signals from the signal processing circuits 11 and 12 are coupled to a central processing unit 13, which may be realized by a microprocessor, with an associated a ROM 22 and a RAM 21.

Preferably, the system illustrated in FIG. 1 includes a monitor/recorder 20, which may provide a visual and- /or audible readout to aid medical personnel providing treatment for the patient. The monitor/recorder 20, as is known, may also effect recording, on strip graphs or the like, of the signals fed to the central processing unit 13, as well as the command signals from the central processing unit, which it generates in response to the physiologic signal(s) and the electrical signal(s) supplied thereto.

The central processing unit 13 provides a number of output command signals, depending on decisions made by the central processing unit 13, under control of its associated RAM 21 and ROM 22. Of course, the central processing unit 13 may elect, without producing any output command signals, to continue monitoring the electrical signal(s) and the physiologic signal(s) from the signal processing circuits 11 and 12, in the event no malfunction of the heart of the patient 10 has been identified.

In the event a malfunction of the heart of the patient 10 is identified by the central processing unit 13, the central processing unit supplies an enabling command signal or signals, depending on the nature of the identified malfunction, to one or another or more than one malfunction correcting means, illustrated as an antitachycardia pacer 14, an antibradycardia pacer 15, a cardioverting apparatus 16, a defibrillating apparatus 17 drug delivery devices 18, and a heart-assist device 19, which may be an assist pump or a similar device. It is to be appreciated that cardioverter and defibrillator may share components and be constructed as illustrated in U.S. Pat. No. 4,774,950.

The malfunction correcting circuits 14–17 produce respective malfunction correcting electrical output signals, which are delivered to the patient 10 as required. The drug delivery devices 19 which may consist of a number of pumps or other drug delivery devices, such as gravity operated delivery systems supply medications to the patient 10 in an effort to overcome or correct the malfunction. The heart-assist device 19, which may be a pump, when energized, aids a patient by assisting pumping action thereby reducing load on the heart or drugs which are supplied to the patient 10 in an effort to overcome the malfunction. These output signals and/or drug(s) and/or the pumping assist are provided to effect termination of, or at least treat in an effective manner, singly or in combination stable SVT, unstable SVT, stable VT, unstable VT, stable atrial fibrillation, unstable atrial fibrillation, ventricular fibrillation, asystole, stable bradycardia, unstable bradycardia, inschemia, early infarction and both stable and unstable heart failure.

Figure 2:
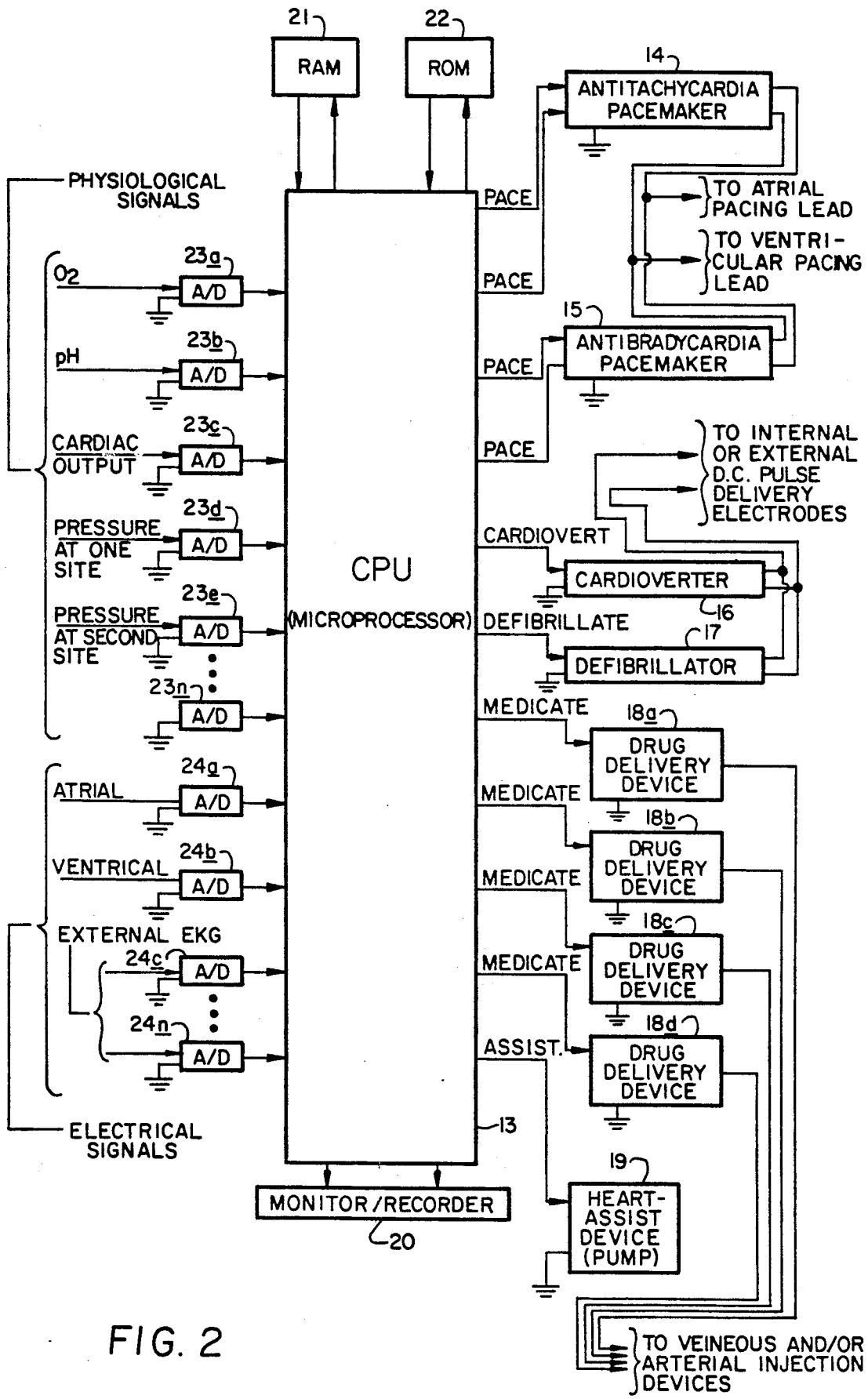
FIG. 2 is a more detailed illustration of the exemplary system for treating a malfunctioning heart and in carrying out the invention in its method aspect.
Figure 3A:
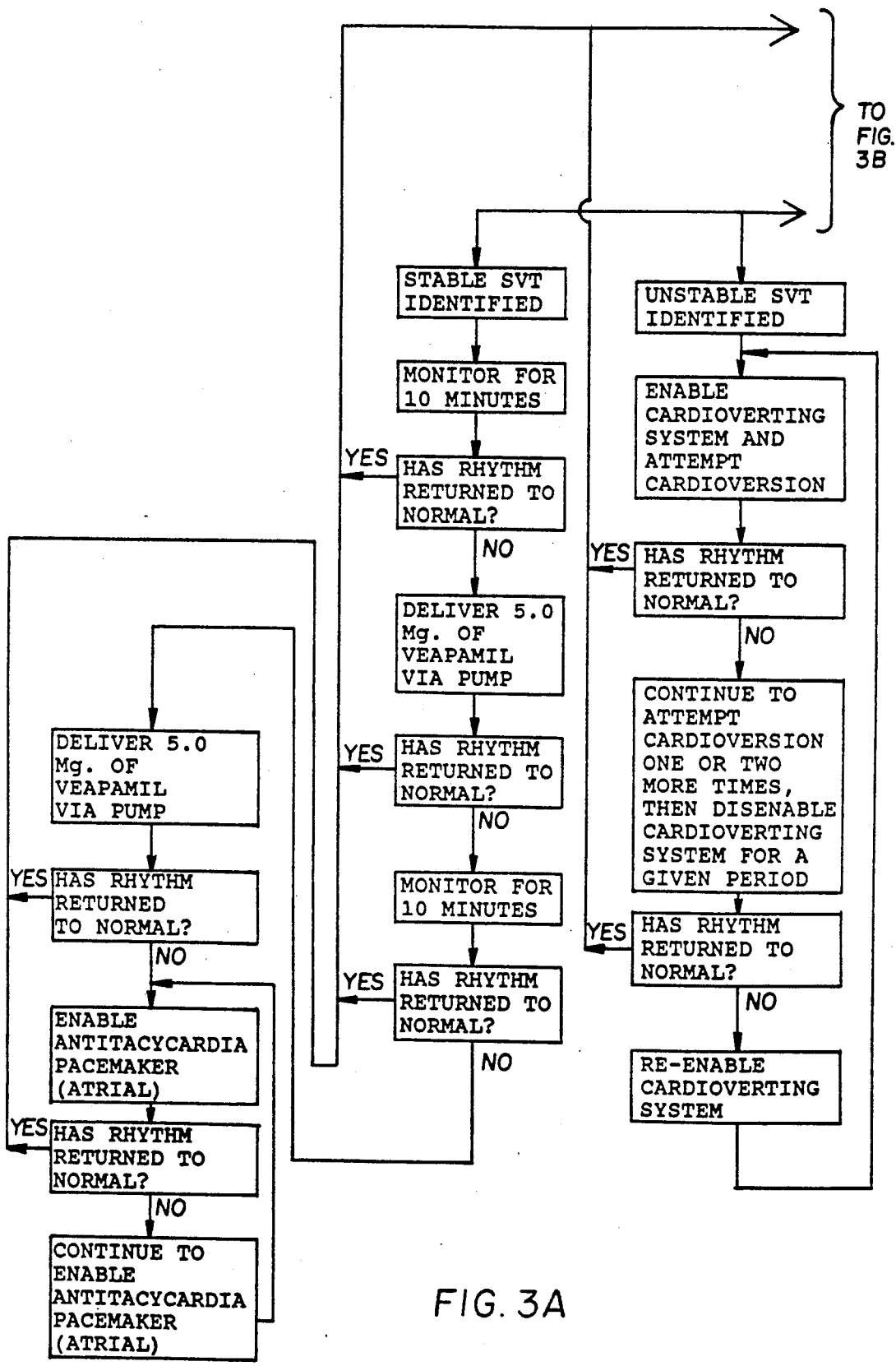
FIGS. 3A–3I, when taken together, constitute a flow chart of steps which may be executed by systems illustrated in FIGS. 1 and 2.
Figure 3B:
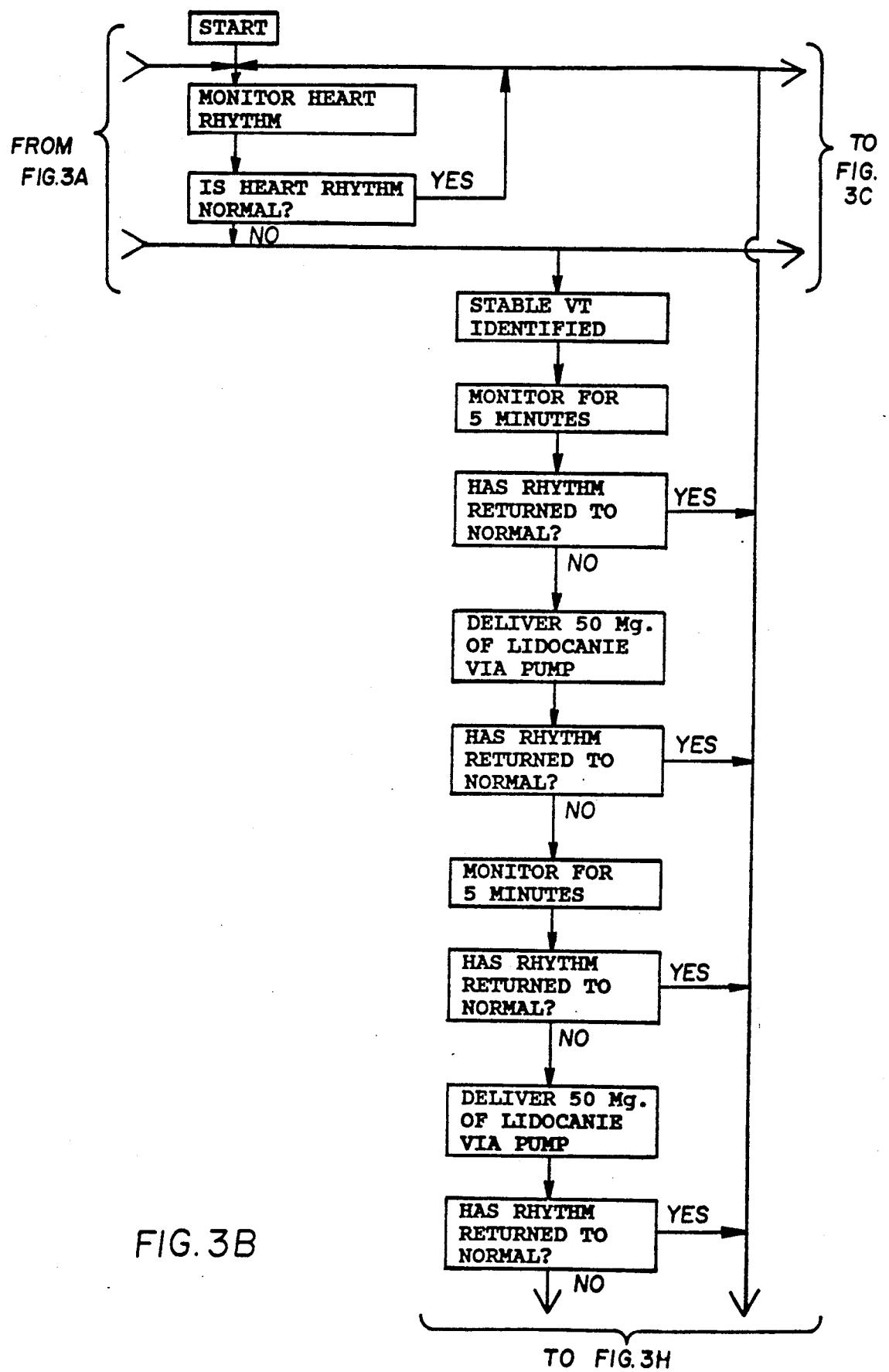
Figure 3C:
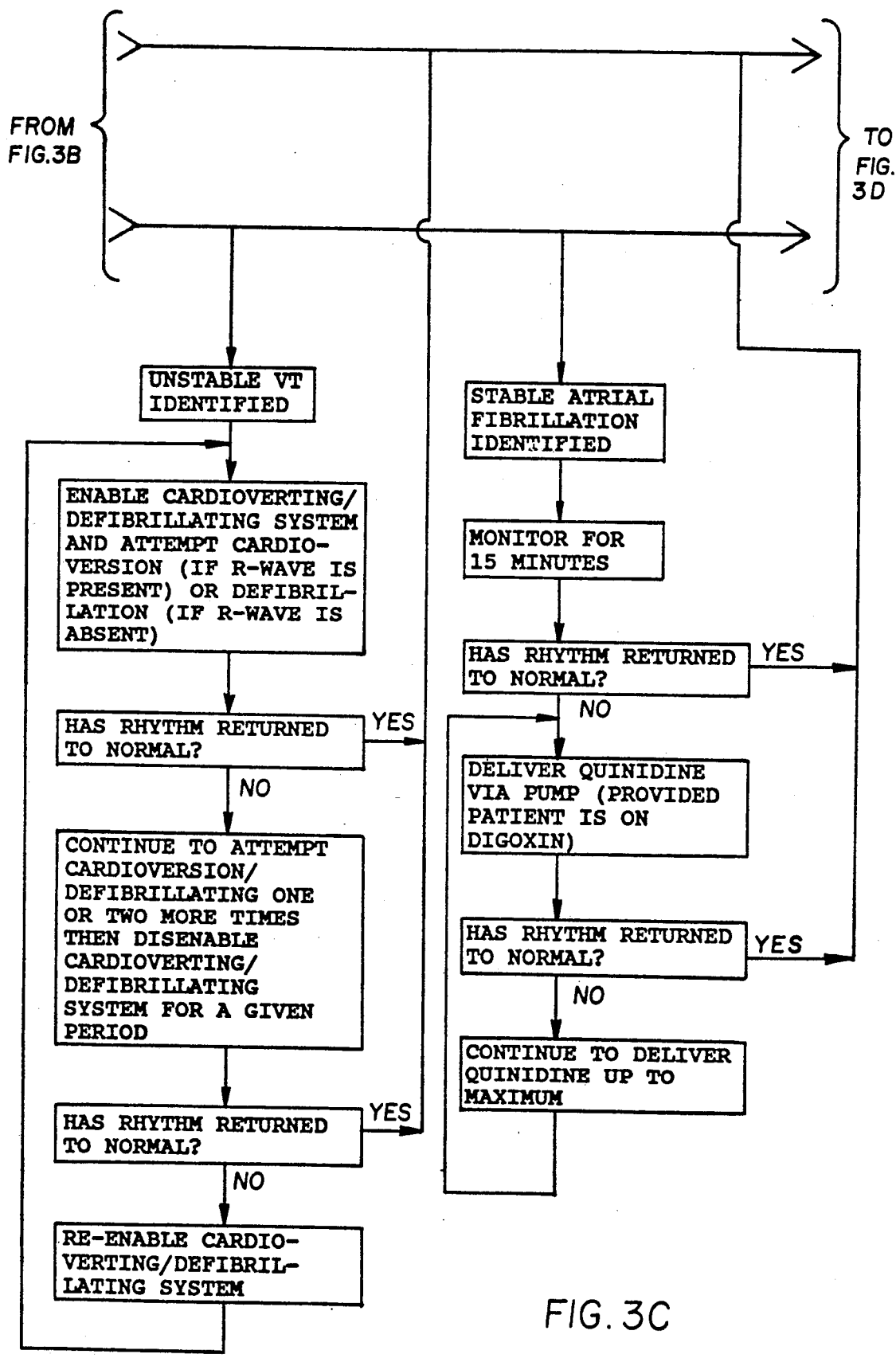
Figure 3D:
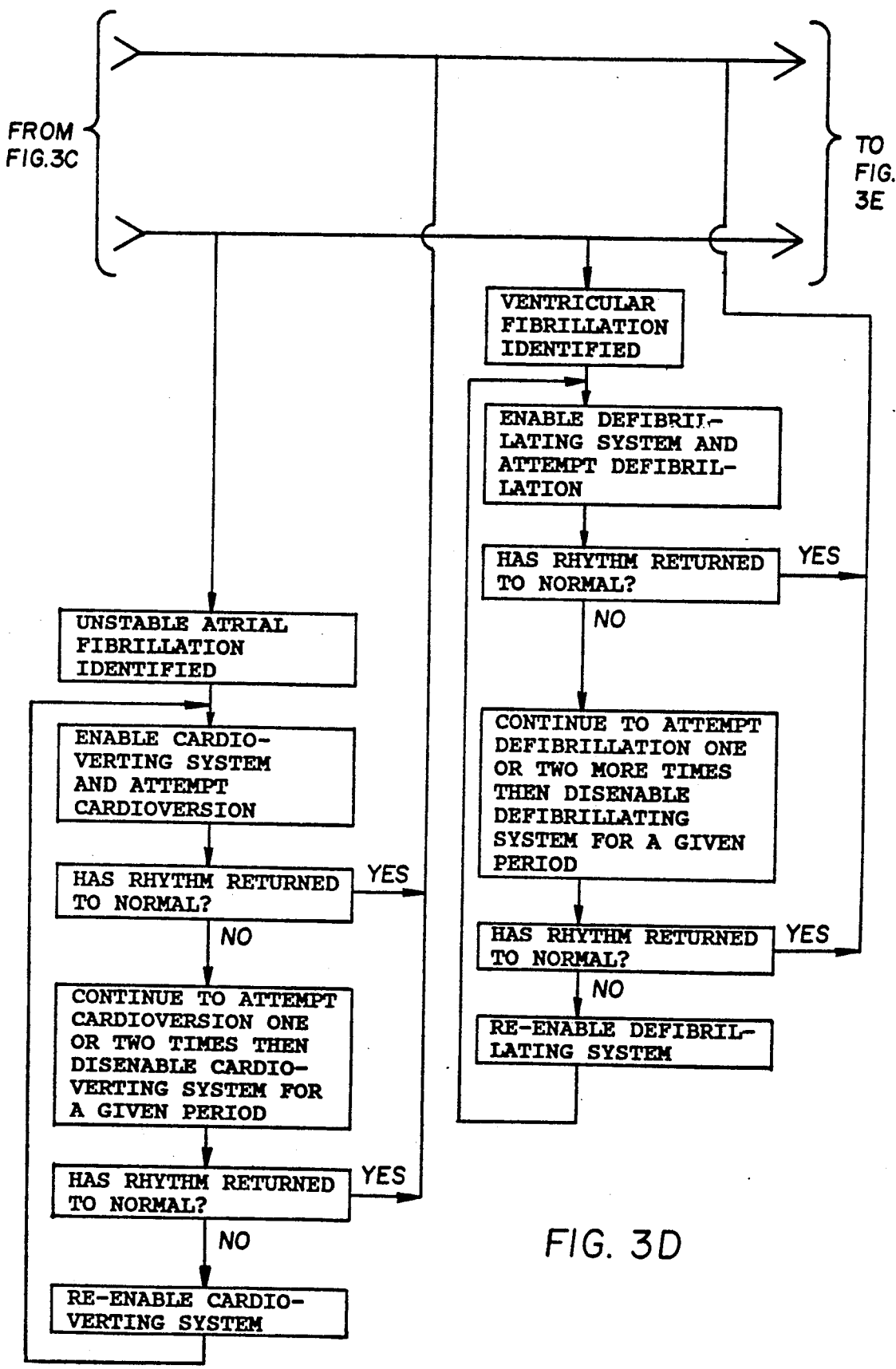
Figure 3E:
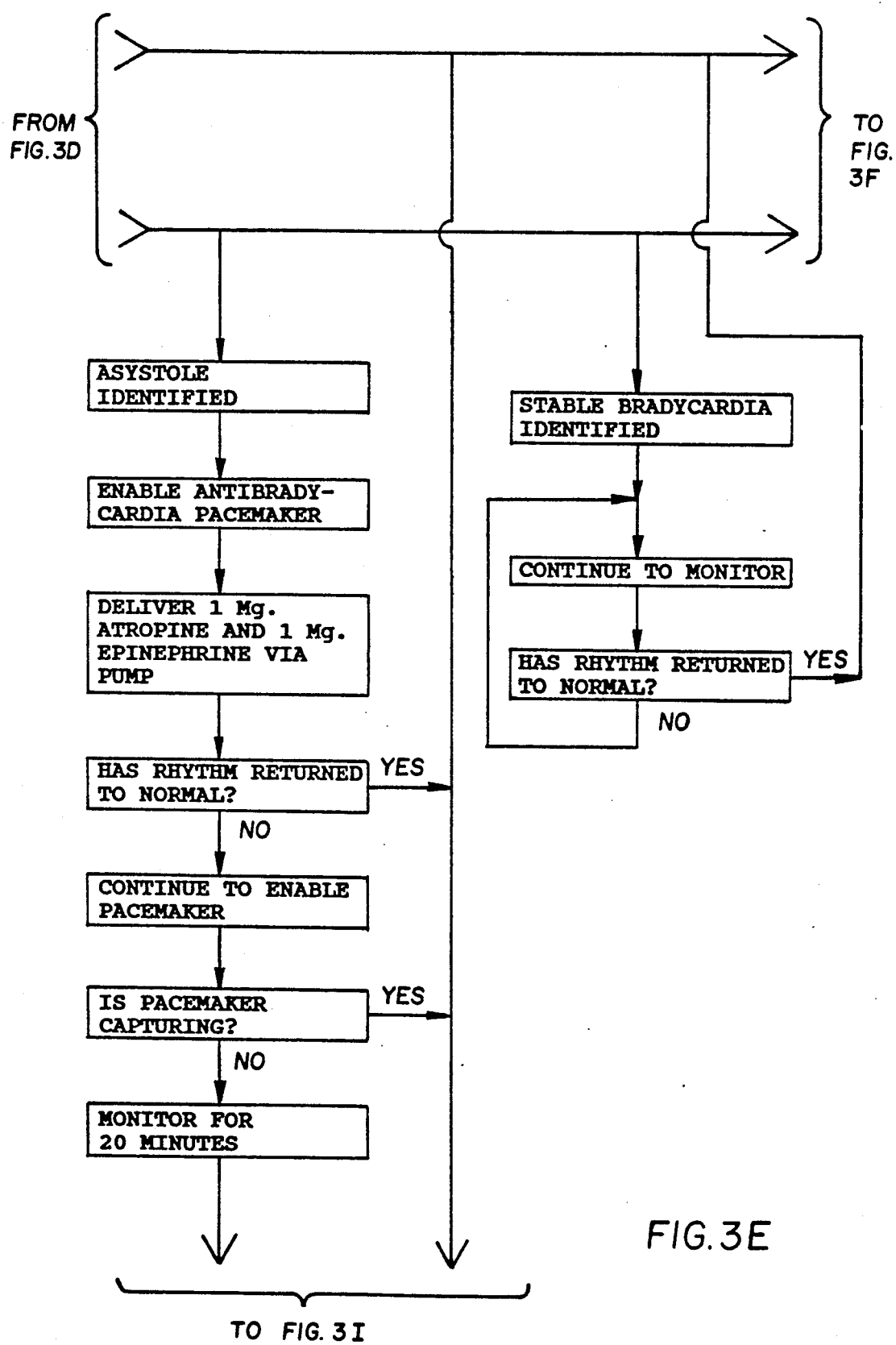
Figure 3F:
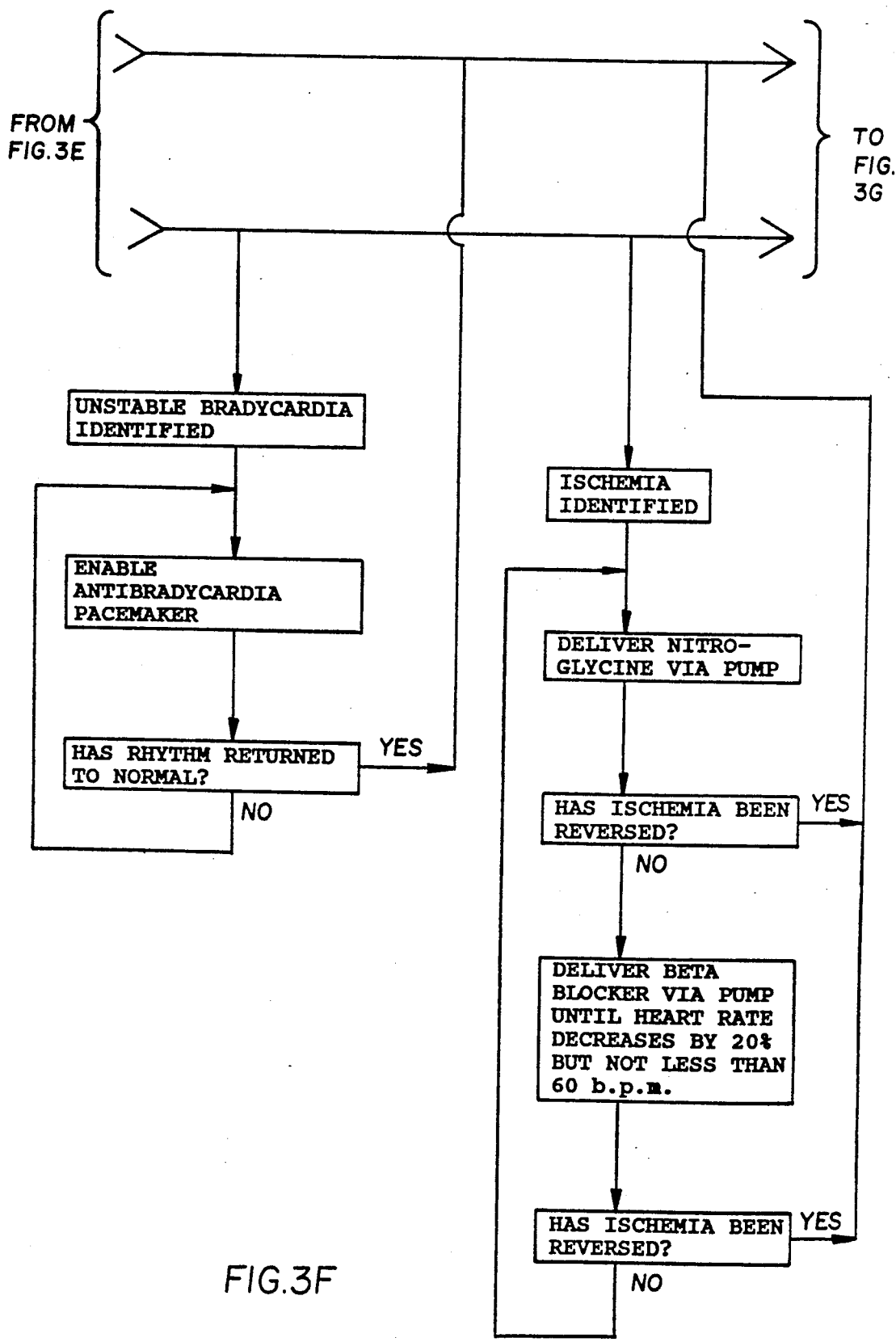
Figure 3G:
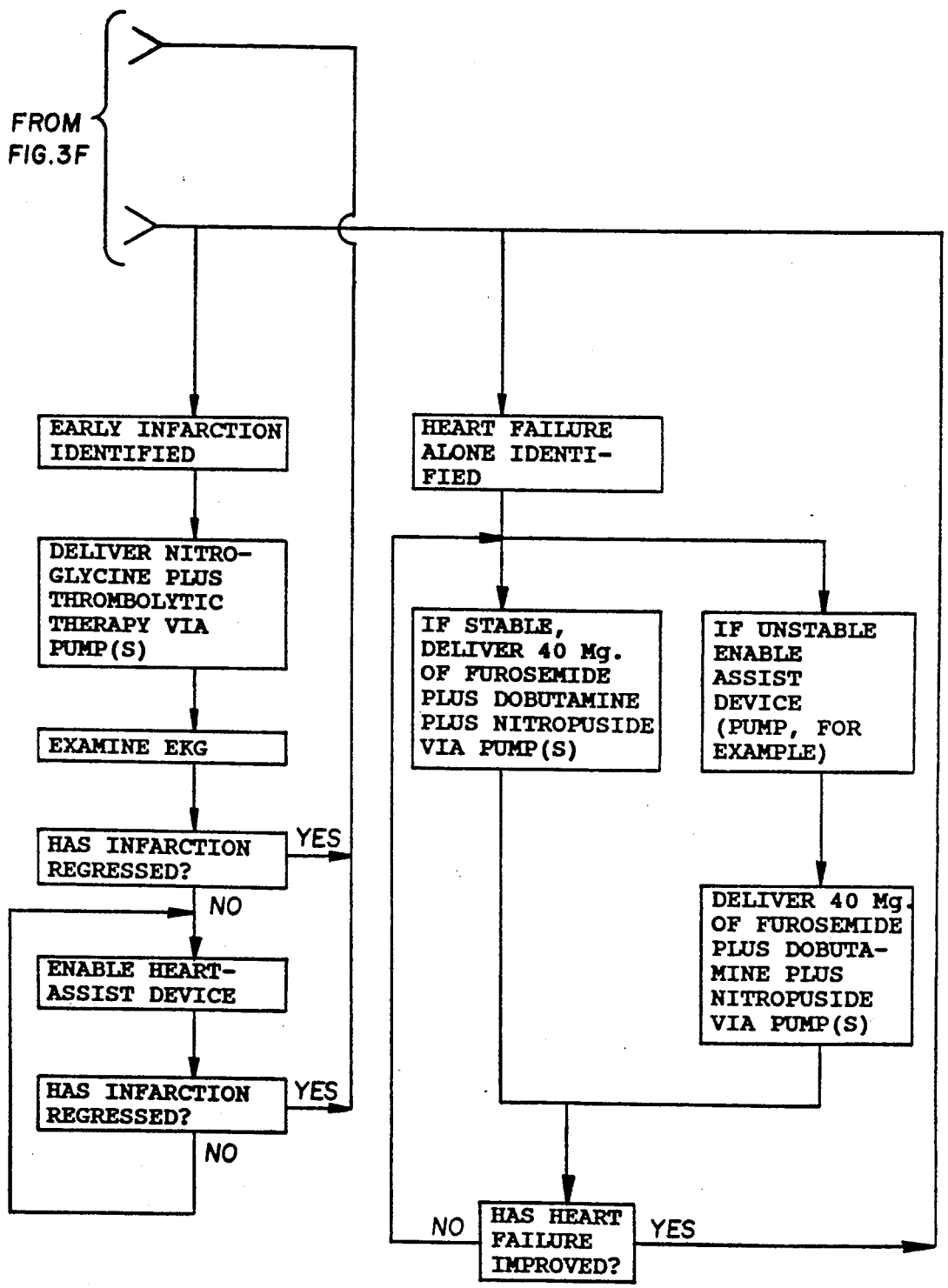
Figure 3H:
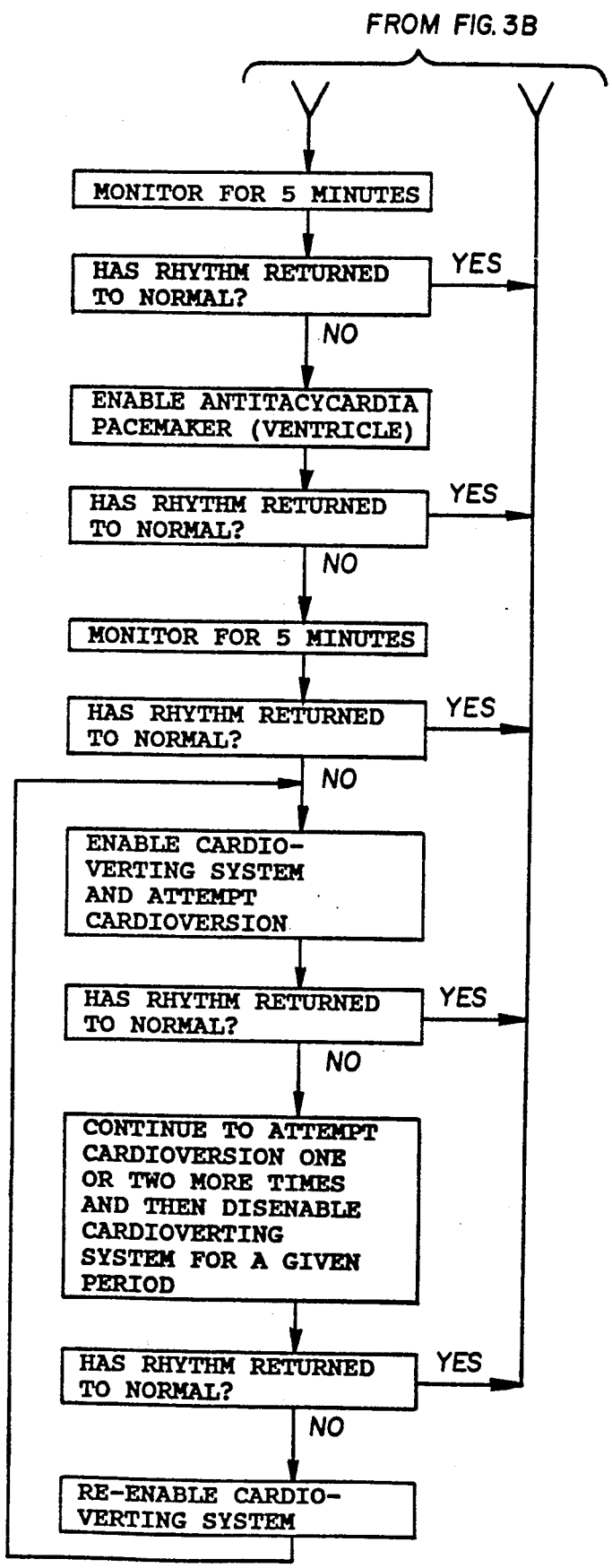
Figure 3I:
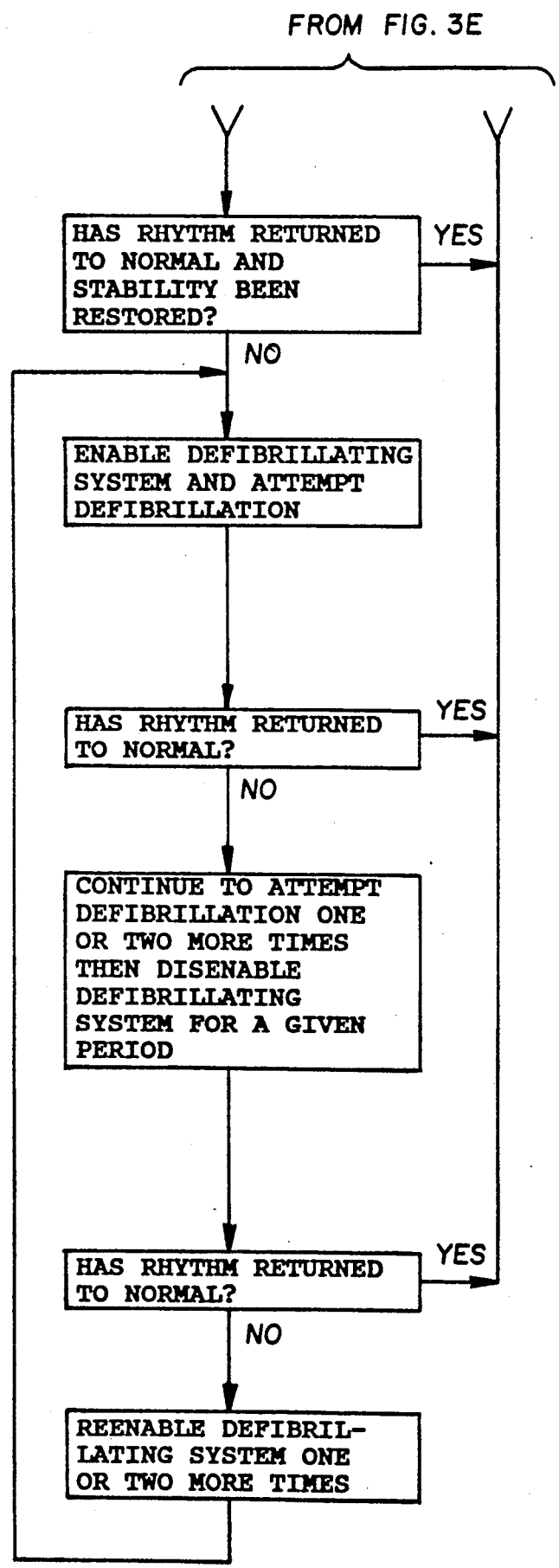
Figure 4:
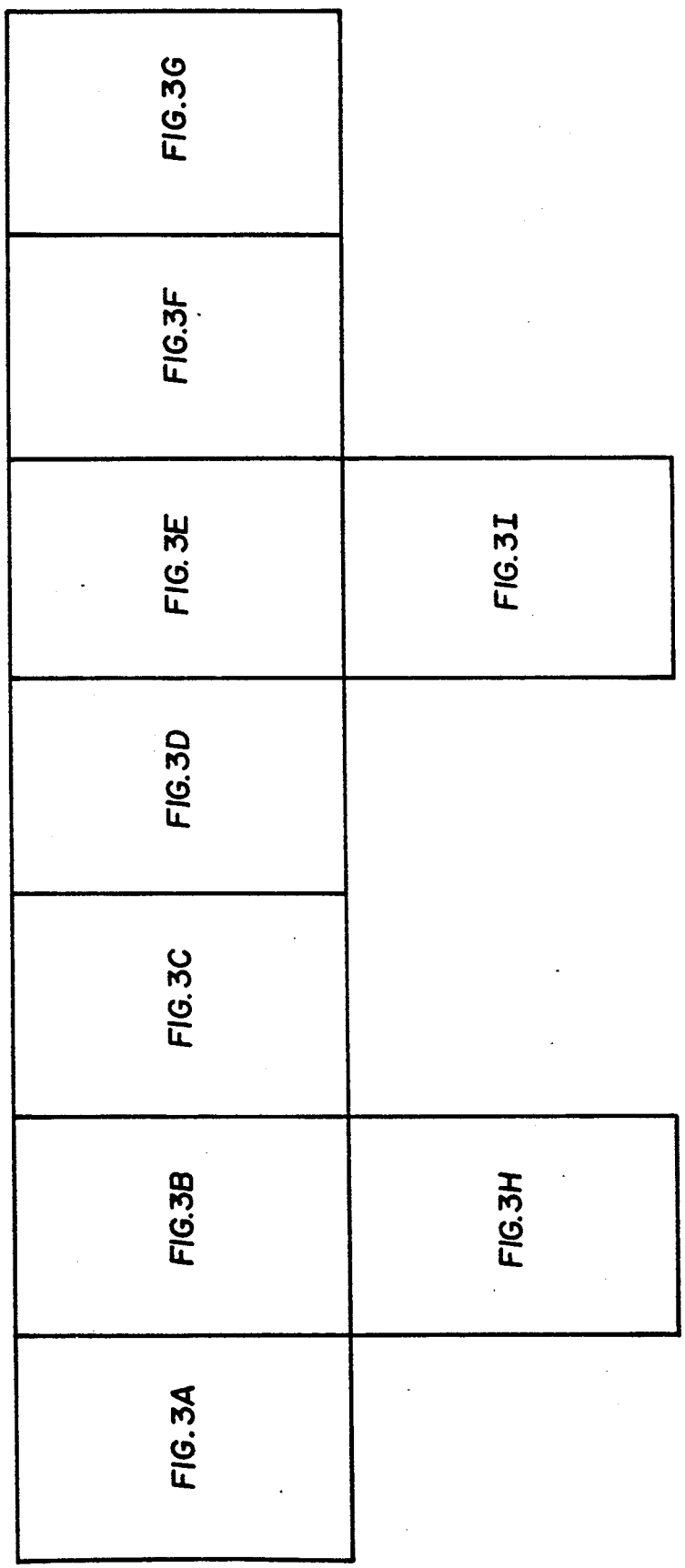
FIG. 4 is a diagrammatic showing of the placement of FIGS. 3A–3I in order to view these figures can be viewed as a whole.

As illustrated in FIG. 2, the preferred embodiment, like the more generalized illustration of FIG. 1, is provided with a CPU 13 and its associated RAM 21 and ROM 22. If desired inputs and outputs to and from the CPU 13 may be fed to a monitor/recorder 20.

The input side of the system, includes a plurality of physiologic signals, actually electric analogue signal representations of physiologic conditions, shown by way of example as $O_2$ level in mixed venous blood, pH of blood, cardiac output, pressure at one site in the circulatory system of the patient and pressure at another site in the circulatory system of the patient. Other possible signals could represent $CO_2$ level in blood, end tidal $CO_2$ level in blood, DP/dt, blood temperature, body temperature, respiratory rate and lactic acidosis, to name a few. The respective physiologic signals are converted into digital signals by respective analogue-to-digital converters 23a to 23n and supplied as distinct inputs to the CPU 13.

The system of FIG. 2 includes electrical signals derived from action of the patient's heart. The electrical signals, as illustrated, include an atrial signal, a ventricular signal and a plurality of EKG signals, which are obtained by conventional means. The respective electrical signal are fed to respective analogue-to-digital converters 24a–24n and are converted into respective digital signals which are fed, as distinct inputs, to the CPU 13.

The CPU 13 effects a comparison of one or more of the digital signal representations of the physiologic signals against a fixed (for example, as disclosed in patent application Ser. No. 233,367) or a varying baseline (for example, as disclosed in U.S. Pat. No. 4,774,950) representations thereof, possibly after processing the signals into signals representing mean, systolic, diastolic, pulse pressures or the like. The CPU 13 also determines the pulse rate, R-wave, QRS complex (possibly against a "template" of the patient's QRS complex when the heart is functioning properly) and/or another morphologic basis, tachycardia acceleration, atrial-ventricular timing, ST segment analysis and the like.

The CPU 13, using programs stored in the ROM 21, determines if any of the malfunctions set out in FIGS. 3A–3G is present and produces control signals which are fed respectively to the antitachycardia pacemaker 14, to the antibradycardia pacemaker 15, to the cardioverter 16, to the defibrillator 17, to the respective drug delivery devices 18a–18d and to the heart-assist device (pump) 19. Each of the pacemakers 14 and 15 receive two possible pacing command signals from the CPU 13, one to effect production of an atrial pacing and the other to effect ventricular pacing. Thus, single or dual chamber pacing is possible when an effort is under way to treat tachycardia or bradycardia.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

I claim:

1. In a system for treating the malfunctioning heart of a patient, the combination of means for deriving at least one electrical signal from the patient's heart, means for deriving at least one physiologic signal from or related to the patient's circulatory system, a central processing unit for controlling delivery of selected heart-malfunction-corrective inputs to the patient, means for inputting the at least one electrical signal and the at least one physiologic signal to the central processing unit, and output means, including defibrillating means, controlled by the central processing unit for providing at least one heart-malfunction-corrective input to the patient from among a plurality of the heart-malfunction-corrective inputs, whereby malfunctions of the heart may be corrected.

2. The combination of claim 1, wherein the output means includes antiachycardia pacing means controlled by the central processing unit.

3. The combination of claim 1, wherein the output means includes antibradycardia pacing means controlled by the central processing unit.

4. The combination of claim 1, wherein the output means includes cardioverting means controlled by the central processing unit.

5. The combination of claim 1, wherein the output means includes drug delivery means controlled by the central processing unit.

6. The combination of claim 1, wherein the output means includes a heart-assist device controlled by the central processing unit.

7. The combination of claim 1, further including monitoring means and/or recording means coupled to the central processing unit for monitoring and/or recording input and output signals to and from the central processing unit.

8. The combination of claim 1, wherein the output means further includes drug delivery means, antiachycardia pacing means, antibradycardia pacing means and cardioverting means controlled by the central processing unit.

9. The combination of claim 1, including means for monitoring heart rhythm to develop the at least one electrical signal, and means responsive to the at least one electrical signal and to the at least one physiologic signal for identifying stable SVT.

10. The combination of claim 1, including means for monitoring heart rhythm to develop the at least one electrical signal, and means responsive to the at least one electrical signal and to the at least one physiologic signal for identifying unstable SVT.

11. The combination of claim 1, including means for monitoring heart rhythm to develop the at least one electrical signal, and means responsive to the at least one electrical signal and to the at least one physiologic signal for identifying stable VT.

12. The combination of claim 1, including means for monitoring heart rhythm to develop the at least one electrical signal, and means responsive to the at least one electrical signal and to the at least one physiologic signal for identifying unstable VT.

13. In a system for treating the malfunctioning heart of a patient, the combination of means for deriving at least one electrical signal from the patient's heart, means for deriving at least one physiologic signal from or related to the patient's circulatory system, a central processing unit for controlling delivery of selected heart-malfunction-corrective inputs to the patient, means for inputting the at least one electrical signal and the at least one physiologic signal to the central processing unit, output means controlled by the central processing unit for providing at least one heart-malfunction-corrective input to the patient from among a plurality of the heart-malfunction-corrective inputs, wherein said means for deriving at least one electrical signal from the patient's heart comprise means for monitoring heart rhythm to develop the at least one electrical signal, and means responsive to the at least one electrical signal and to the at least one physiologic signal for identifying stable atrial fibrillation, whereby malfunctions of the heart may be connected.

14. In a system for treating the malfunctioning heart of a patient, the combination of means for deriving at least one electrical signal from the patient's heart, means for deriving at least one physiologic signal from or related to the patient's circulatory system, a central processing unit for controlling delivery of selected heart-malfunction-corrective inputs to the patient, means for inputting the at least one electrical signal and the at least one physiologic signal to the central processing unit, output means controlled by the central processing unit for providing at least one heart-malfunction-corrective input to the patient from among a plurality of the heart-malfunction-corrective inputs, wherein said means for deriving at least one electrical signal from the patient's heart comprise means for monitoring heart rhythm to develop the at least one electrical signal, and means responsive to the at least one electrical signal and to the at least one physiologic signal for identifying unstable atrial fibrillation, whereby malfunctions of the heart may be corrected.

15. In a system for treating the malfunctioning heart of a patient, the combination of means for deriving at least one electrical signal from the patient's heart, means for deriving at least one physiologic signal from or related to the patient's circulatory system, a central processing unit for controlling delivery of selected heart-malfunction-corrective inputs to the patient, means for inputting the at least one electrical signal and the at least one physiologic signal to the central processing unit, output means controlled by the central processing unit for providing at least one heart-malfunction-corrective input to the patient from among a plurality of the heart-malfunction-corrective inputs, wherein said means for deriving at least one electrical signal from the patient's heart comprise means for monitoring heart rhythm to develop the at least one electrical signal, and means responsive to the at least one electrical signal and to the at least one physiologic signal for identifying ventricular fibrillation, whereby malfunctions of the heart may be corrected.

16. The combination of claim 1, including means for monitoring heart rhythm to develop the at least one electrical signal, and means responsive to the at least one electrical signal and to the at least one physiologic signal for identifying asystole.

17. The combination of claim 1, including means for monitoring heart rhythm to develop the at least one electrical signal, and means responsive to the at least one electrical signal and to the at least one physiologic signal for identifying stable bradycardia.

18. The combination of claim 1, including means for monitoring heart rhythm to develop the at least one electrical signal, and means responsive to the at least one electrical signal and to the at least one physiologic signal for identifying unstable bradycardia.

19. The combination of claim 1, including means for monitoring heart rhythm to develop the at least one electrical signal, and means responsive to the at least one electrical signal and to the at least one physiologic signal for identifying ischemia.

20. The combination of claim 1, including means for monitoring heart rhythm to develop the at least one electrical signal, and means responsive to the at least one electrical signal and to the at least one physiologic signal for identifying early infarction.

21. The combination of claim 1, including means for monitoring heart rhythm to develop the at least one electrical signal, and means responsive to the at least one electrical signal and to the at least one physiologic signal for identifying heart failure alone.

22. The combination of claim 1, including means for monitoring heart rhythm to develop the at least one electrical signal, and means responsive to the at least one electrical signal and to the at least one physiologic signal for identifying stable SVT, unstable SVT, stable VT, unstable VT, stable atrial fibrillation, unstable atrial fibrillation, ventricular fibrillation, asystole, stable bradycardia, unstable bradycardia, ischemia, early infarction and heart failure alone.

23. In a system for treating the malfunctioning heart of a patient, the combination of means for deriving at least one electrical signal from the patient's heart, means for deriving, at least one physiologic signal from or related to the patient's circulatory system, a central processing unit, means for inputting the at least one electrical signal and the at least one physiologic signal to the central processing unit, and output means, includes defibrillating means, controlled by the central processing unit for providing at least one heart-malfunction-corrective input to the patient from a plurality of heart-malfunction-corrective inputs, whereby malfunctions of the heart may be corrected.

24. The system according to claim 23, wherein said output means includes cardioverting means controlled by the central processing unit for providing another heart-malfunction-corrective input to the patient.

25. The system according to claim 23, wherein said output means includes antitachycardia pacing means controlled by the central processing unit for providing at least one heart-malfunction-corrective antitachycardia pacing input to the patient.

26. The system according to claim 23, wherein said output means includes at least one heart-assist device controlled by the central processing unit for providing another heart-malfunction-corrective input to the patient.

27. The system according to claim 23, wherein said output means includes antibradycardia pacing means controlled by the central processing input for providing a heart-malfunction-corrective pacing input to the patient.

28. The system according to claim 23, wherein said output means includes at least one drug delivery device controlled by the central processing unit for providing at least one heart-malfunction-corrective drug input to the patient.

29. In a system for treating the malfunctioning heart of a patient, the combination of means for monitoring heart rhythm to develop at least one electrical signal from the patient's heart, means for deriving at, least one physiologic signal from or related to the patient's circulatory system, a central processing unit including means for identifying malfunctions of the heart including stable atrial fibrillation, means for inputting the at least one electrical signal and the at least one physiologic signal to the central processing unit as a basis for identifying malfunctions of the heart including stable atrial fibrillation, and output means controlled by the central processing unit for providing at least one heart-malfunction-corrective input to the patient, whereby malfunctions of the heart including stable atrial fibrillation may be corrected.

30. The system according to claim 29, wherein said output means includes cardioverting means controlled by the central processing unit for providing another heart-malfunction-corrective input to the patient.

31. The system according to claim 29, wherein said output means includes antiachycardia pacing means controlled by the central processing unit for providing at least one heart-malfunction-corrective antitachycardia pacing input to the patient.

32. The system according to claim 29, wherein said output means includes at least one heart-assist device controlled by the central processing unit for providing another heart-malfunction-corrective input to the patient.

33. The system according to claim 29, wherein said output means includes antibradycardia pacing means controlled by the central processing unit for providing a heart-malfunction-corrective pacing input to the patient.

34. The system according to claim 29, wherein said output means includes at least one drug delivery device controlled by the central processing unit for providing at least one heart-malfunction-corrective drug input to the patient.

35. In a system for treating the malfunctioning heart of a patient, the combination of means for monitoring heart rhythm to develop at least one electrical signal from the patient's heart, means for deriving at least one physiologic signal from or related to the patient's circulatory system, a central processing unit including means for identifying malfunctions of the heart including unstable atrial fibrillation, means for inputting the at least one electrical signal and the at least one physiologic signal to the central processing unit as a basis for identifying malfunctions of the heart including unstable atrial fibrillation, and output means controlled by the central processing unit for providing at least one heart-malfunction-corrective input to the patient, whereby malfunctions of the heart including unstable atrial fibrillation may be corrected.

36. The system according to claim 35, wherein said output means includes cardioverting means controlled by the central processing unit for providing another heart-malfunction-corrective input to the patient.

37. The system according to claim 35, wherein said output means includes antitachycardia pacing means controlled by the central processing unit for providing at least one heart-malfunctioned-corrective antitachycardia pacing input to the patient.

38. The system according to claim 35, wherein said output means includes at least one heart-assist device controlled by the central processing unit for providing another heart-malfunction-corrective input to the patient.

39. The system according to claim 35, wherein said output means includes antibradycardia pacing means controlled by the central processing unit for providing a heart-malfunction-corrective pacing input to the patient.

40. The system according to claim 35, wherein said output means includes at least one drug delivery device controlled by the central processing unit for providing at least one heart-malfunction-corrective drug input to the patient.

41. In a system for treating the malfunctioning heart of a patient, the combination of means for monitoring heart rhythm to develop at least one electrical signal from the patient's heart, means for deriving at least one physiologic signal from or related to the patient's circulatory system, a central processing unit including means for identifying malfunctions of the heart including ventricular fibrillation, means for inputting the at least one electrical signal and the at least one physiologic signal to the central processing unit as a basis for identifying heart malfunctions including ventricular fibrillation, and output means controlled by the central processing unit for providing at least one heart-malfunction-corrective input to the patient, whereby malfunctions of the heart including ventricular fibrillation may be corrected.

42. The system according to claim 41, wherein said output means includes cardioverting means controlled by the central processing unit for providing another heart-malfunction-corrective input to the patient.

43. The system according to claim 41, wherein said output means includes antitachycardia pacing means controlled by the central processing unit for providing at least one heart-malfunction-corrective antitachycardia pacing input to the patient.

44. The system according to claim 41, wherein said output means includes at least one heart-assist device controlled by the central processing unit for providing another heart-malfunction-corrective input to the patient.

45. The system according to claim 41, wherein said output means includes antibradycardia pacing means controlled by the central processing unit for providing a heart-malfunction-corrective pacing input to the patient.

46. The system according to claim 44, wherein said output means includes at least one drug delivery device controlled by the central processing unit for providing at least one heart-malfunction-corrective drug input to the patient.

47. In a system for treating the malfunctioning heart of a patient, the combination of means for deriving at least one EKG signal from the patient, means for deriving at least one physiologic signal from or related to the patient's circulatory system, a central processing unit for controlling delivery of selected heart-malfunction-corrective inputs to the patient, means for inputting the at least one EKG signal and the at least one physiologic signal to the central processing unit, and output means, including defibrillating means, controlled by the central processing unit for providing at least one heart-malfunction-corrective input to the patient from among a plurality of the heart-malfunction-corrective inputs, whereby malfunctions of the heart may be corrected.

48. In a system for treating the malfunctioning heart of a patient, the combination of means for deriving at least one EKG signal from the patient, means for deriving at least one physiologic signal from or related to the patient's circulatory system, a central processing unit for controlling delivery of selected heart-malfunction-corrective inputs to the patient, means for inputting the at least one EKG signal and the at least one physiologic signal to the central processing unit, output means controlled by the central processing unit for providing at least one heart-malfunction-corrective input to the patient from among a plurality of the heart-malfunction-corrective inputs, wherein said means for deriving at least one EKG signal from the patient comprise means for monitoring heart rhythm to develop the at least one EKG signal, and means responsive to the at least one EKG signal and to the at least one physiologic signal for identifying stable atrial fibrillation, whereby malfunctions of the heart may be corrected.

49. In a system for treating the malfunctioning heart of a patient, the combination of means for deriving at least one EKG signal from the patient, means for deriving at least one physiologic signal from or related to the patient's circulatory system, a central processing unit for controlling delivery of selected heart-malfunction-corrective inputs to the patient, means for inputting the at least one EKG signal and the at least one physiologic signal to the central processing unit, output means controlled by the central processing unit for providing at least one heart-malfunction-corrective input to the patient from among a plurality of the heart-malfunction-corrective inputs, wherein said means for deriving at least one EKG signal from the patient comprise means for monitoring heart rhythm to develop the at least one EKG signal, and means responsive to the at least one EKG signal and to the at least one physiologic signal for identifying unstable atrial fibrillation, whereby malfunctions of the heart may be corrected.

50. In a system for treating the malfunctioning heart of a patient, the combination of means for deriving at least one EKG signal from the patient, means for deriving at least one physiologic signal from or related to the patient's circulatory system, a central processing unit for controlling delivery of selected heart-malfunction-corrective inputs to the patient, means for inputting the at least one EKG signal and the at least one physiologic signal to the central processing unit, output means controlled by the central processing unit for providing at least one heart-malfunction-corrective input to the patient from among a plurality of the heart-malfunction-corrective inputs, wherein said means for deriving at least one EKG signal from the patient comprise means for monitoring heart rhythm to develop the at least one EKG signal, and means responsive to the at least one EKG signal and to the at least one physiologic signal for identifying ventricular fibrillation, whereby malfunctions of the heart may be corrected.

51. In a system for treating the malfunctioning heart of a patient, the combination of means for deriving at least one EKG signal from the patient, means for deriving at, least one physiologic signal from or related to the patient's circulatory system, a central processing unit, means for inputting the at least one EKG signal and the at least one physiologic signal to the central processing unit, and output means including defibrillating means controlled by the central processing unit for providing at least one heart-malfunction-corrective input to the patient from a plurality of heart-malfunction-corrective inputs, whereby malfunctions of the heart including fibrillation may be corrected.

52. In a system for treating the malfunctioning heart of a patient, the combination of means for monitoring heart rhythm to develop at least one EKG signal from the patient, means for deriving at least one physiologic signal from or related to the patient's circulatory system, a central processing unit including means for identifying malfunctions of the heart including stable atrial fibrillation, means for inputting the at least one EKG signal and the at least one physiologic signal to the central processing unit as a basis for identifying malfunctioning of the heart including stable atrial fibrillation, and output means controlled by the central processing unit for providing at least one heart-malfunction-corrective input to the patient, whereby malfunctions of the heart including stable atrial fibrillation may be corrected.

53. In a system for treating the malfunctioning heart of a patient, the combination of means for monitoring heart rhythm to develop at least one EKG signal from the patient, means for deriving at least one physiologic signal from or related to the patient's circulatory system, a central processing unit including means for identifying malfunctions of the heart including unstable atrial fibrillation, means for inputting the at least one EKG signal and the at least one physiologic signal to the central processing unit as a basis for identifying malfunctions of the heart including unstable atrial fibrillation, and output means controlled by the central processing unit for providing at least one heart-malfunction-corrective input to the patient, whereby malfunctions of the heart including unstable atrial fibrillation may be corrected.

54. In a system for treating the malfunctioning heat of a patient, the combination of means for monitoring heart rhythm to develop at least one EKG signal from the patient, means for deriving at least one physiologic signal from or related to the patient's circulatory system, a central processing unit including means for identifying malfunctions of the heart including ventricular fibrillation, means for inputting the at least one EKG signal and the at least one physiologic signal to the central processing unit as a basis for identifying heart malfunctions including ventricular fibrillation, and output means controlled by the central processing unit for providing at least one heart-malfunction-corrective input to the patient, whereby malfunctions of the heart including ventricular fibrillation may be corrected.

* * * * *